US005178862A

United States Patent [19]

Olsen

[11] Patent Number: 5,178,862
[45] Date of Patent: Jan. 12, 1993

[54] CANINE DISTEMPER VIRUS VACCINE AND METHOD OF PREPARATION

[75] Inventor: Richard G. Olsen, London, Ohio

[73] Assignee: Parhelion Corporation, Columbus, Ohio

[21] Appl. No.: 444,525

[22] Filed: Dec. 1, 1989

[51] Int. Cl.[5] .......................... A61K 39/12; C12N 5/00

[52] U.S. Cl. ........................................ 424/89; 424/88; 530/350; 530/395; 435/69.3; 435/70.1; 435/70.3; 435/239; 435/240.1; 435/240.3

[58] Field of Search .................... 424/89, 88; 530/350, 530/395; 435/69.3, 70.1, 70.3, 239, 240.1, 240.3

[56] References Cited

U.S. PATENT DOCUMENTS 3,836,626 9/1974 Lavender et al. .................... 424/89
4,434,157 2/1984 Olsen .................................... 424/89
4,992,272 2/1991 Bass et al. ............................ 424/89

*Primary Examiner*—Johnnie R. Brown
*Assistant Examiner*—Abdel A. Mohamed
*Attorney, Agent, or Firm*—Mueller and Smith

[57] ABSTRACT

Disclosed is a vaccine for the prevention of disease caused by canine distemper virus (CDV). The vaccine is prepared from CDV immunogens derived from CDV persistently-infected cells cultured in vitro. CCL-64 mink lung cells are the preferred cell line. CDV persistently-infected cells are cultured in serum-containing growth medium, the cells transferred and maintained in serum-free medium under conditions and for a time adequate to accumulate in said serum-free medium said CDV immunogens, and the cells separated from said CDV immunogen-containing supernatant. The CDV vaccine is made by diluting said supernatent and blending with a pharmaceutically-acceptable adjuvant.

9 Claims, No Drawings

CANINE DISTEMPER VIRUS VACCINE AND METHOD OF PREPARATION

BACKGROUND OF THE INVENTION

Canine distemper virus (CDV) belongs to the family Paramyxoviridae within the genus Morbillivirus. CDV is an enveloped single-stranded RNA virus of about 100-300 nm in diameter. The CDV virion core contains a nucleoprotein (NP) peptide that closely associated with viral RNA. A second core peptide is a phenophorylase (P). The CDV envelope contains three peptides, M protein (matrix protein) and two glycoproteins. The glycoproteins are the hemagglutinin glycoproteins (H) and a fusion (F) glycoprotein. The fusion glycoprotein is degraded into smaller sub-units designated $F_1$ and $F_2$. The H protein is responsible for viral adsorption to target cells and the fusion glycoprotein is responsible for the cell-to-cell fusion. As far as is known, all distemper virus isolates contain these common viral polypeptides. The route of infection to the dog is by infective aerosol droplets. Transmission of the virus is facilitated by coughing and sneezing and close confinement in a warm, humid, closed environment. Studies suggest that viral infection occurs first in the respiratory epithelium of the upper oronasal tract with subsequent spread to the deep pulmonary parenchyma. Gorham "Canine Distemper", *Advance Veterinary Science*, Brandley and Jungher Editors, 6:288-315 (1960).

Tissue macrophages and monocytes located in or along respiratory epithelium in tonsils appear to be the first cell type to pick up and replicate CDV. The virus then is spread by lymphatics in blood to distant lymphoreticular tissues. This is accomplished by viremia and occurs anywhere from two to four days after initial infection. Between eight and nine days after infection, the virus spreads beyond lymphoreticular tissues to involve epithelial and mesenchymal tissues. Appel, "Pathogenesis of Canine Distemper", *The Am. J. Vet. Res.*, 30:1167-1182 (1969). This probably occurs in every animal regardless of the outcome of the disease process. It is at this stage of the virus infection that specific host immune responses to viral antigens influence the outcome of disease. The acute fatal form of the disease is characterized by unrestricted viral spread to virtually every tissue in the body. Virus is found in every excretion and secretion and, by using immunofluorescence methods or antigen tracing techniques, antigen can be demonstrated in virtually every cell type within the dog. For most of these animals, the most likely cause of death is fulminant fatal neurologic involvement.

Some CDV infected dogs exhibit clinically delayed progression of disease and modest convalescent immune responses. Clinical signs, if present, are subtle early in the disease and are a reflection of viral persistence within the central nervous system (CNS). Subsequent development over CNS disease is variable. Most CDV infected dogs exhibit essentially no overt clinical signs of disease and are recognized as convalescent, clinically normal dogs. Actively infected dogs destined to recover from CDV infection will demonstrate free circulating anti-viral antibodies on or about post infection day six or seven. Krakowka, et al., "Serologic Response to Canine Distemper Viral Antigens in Gnotobiotic Dogs Infected with R-252 Canine Distemper Virus", *J. Infect. Dis.*, 132:384-392 (1975). Titers rise rapidly to high levels in early convalescence.

Dogs affected acutely with CDV show variable degrees of depression, anorexia, and fever. The skin may be variably dehydrated, dry-roughened, and inelastic. A proportion of these animals will show photophobia and some will have evidence of mucopurulent ocular-nasal discharge. Intermittent diarrhea is a common clinical sign. During this acute viremic phase of the disease, virus is shed in every secretion and excretion. As the disease progresses, pneumonia, frequently due to secondary bacterial invaders, may develop. Dogs in this stage of disease are moderately to severely lymphopenic. They frequently exhibit a coincidental leukocytosis and left shift, depending on the degree or amount of secondary infection.

Although acutely affected dogs can show virtually every combination of neurological signs, in its most common presentation a dog presents petit mal or grand mal siezures. These convulsive episodes occur over time and with increasing frequency.

The second neurologic form of canine distemper is that which occurs with old dog encephalitis (ODE), or occurs after sub-clinical infection and apparent recovery. The CNS signs can be extremely varied in presentation and can be mistaken for brain tumor, head trauma, bacterial menengitis, hydrocephalus, and spinal cord disk disease. A major non-neural manifestation of CDV infection in dogs is CDV-associated immunodepression. Krakowka, et al., "Canine Distemper Virus: A Review of Structural and Functional Modulations in Lymphoid Tissues", *Am. J. Vet. Res.*, 41:284-292 (1980). Many of the signs of canine distemper virus infection are attributable to coincidental secondary infectious processes occurring in this debilitated animal.

The chief and most important bacterial pathogens associated with disease in dogs are the pneumonic bacterial species including: *Bordetella bronchiseptica*, Pasteurella spp., and of course, Staphylococcus and Streptococcus spp. These agents are responsible for the purulent conjuctivitus, rhinitis, and bronchopneumonia noted clinically in CDV-infected dogs. Mixed viral infections, chiefly of the respiratory type, also are common. In addition to canine adenovirus II infection, reovirus, canine parainfluenza virus, and presumably other viruses such as canine herpes virus, are all involved in this dual or multiple mixed infection problem.

As a consequence of direct CDV infection either in lymphoid cells and/or macrophages, lymphocytes from CDV-infected dogs are rendered incapable of generating effective in vitro and in vivo immune responses. The early virolytic effects of CDV upon the lymphoid system and macrophages also has the effect of suppressing established immune responses and/or normal host defenses.

There exists a number of safe and efficacious, modified-live viral vaccine products. The virus, consisting chiefly of laboratory adapted and attenuated Rockborn or Lederle strains of CDV, is propagated in canine origin continuous cell lines. One innoculation into the CDV-susceptible clinically healthy, normal dog, will provide effective and probably lifelong immunity. Thus, under typical clinical circumstances, immunity can be assured by delivering the product according to manufacturer's instructions to the animal or animals in question. There are, however, a number of different exceptions to this generality that should be mentioned. For example, the use of modified-live CDV vaccine in exotic animal species should be avoided. Montali, et al., "Clinical Trials with Canine Distemper Vaccines in Exotic Carnivores", *J. Am. Vet. Med. Assoc.*, 183:1163–1167 (1983). Some exotics such as the lesser panda and black-footed ferret are highly susceptible to CDV and have been killed with modified-live (MLV) CDV vaccine. Even species within the Canidae family may show heightened susceptibility to CDV. For example, MLV-CDV was recently shown to be dangerous for use in grey foxes but not in red foxes. Halbrooks, et al, "Response of Grey Foxes to Modified-live Virus Canine Distemper Vaccines", *J. Am. Vet. Med. Assoc.*, 179:1170–1174 (1981).

The final precaution relates to the clinical interaction of canine parvovirus infection with canine distemper virus infection. On a clinical basis, it has been noticed that canine parvovirus infection potentiates the lethal effects of either concurrent CDV infection or CDV fatalities associated with vaccination with an ordinarily safe modified-live product. Though this is a clinical association, it is known that dogs actively infected with virulent canine parvovirus are at risk for developing fatal CDV-vaccine associated neurologic disease. Krakowka, et al, "Canine Parvovirus Infection Potentiates Canine Distemper Encephalitis due to Modified-live Virus Vaccine", *J. Am. Vet. Res. Assoc.*, 180:137–139 (1982).

Thus, there is a current need for an efficacious non-infective CDV vaccine product that can be used in combination with the ML-CPV vaccine. It is to such a vaccine that the present invention is directed.

BROAD STATEMENT OF THE INVENTION

One aspect of the present invention comprises a vaccine for the prevention of disease caused by canine distemper virus (CDV). Such vaccine comprises adjuvant-containing, serum-free first medium-containing CDV viral precursor immunogens derived from serum-containing medium in vitro grown CCL-64 mink lung cells persistently-infected with CDV virus wherein said viral (precursor) immunogens are harvested from said persistently-infected cells (CCL-64-LyCDV) which have been transferred to serum-free second growth medium. Another aspect of the present invention comprises the CDV-infected mink lung cell line PH-2 or CCL-64-LyCDV (ATCC Accession No. CRL 9891).

The CDV viral precursor immunogen-based vaccine of the present invention is made by culturing CCL-64-LyCDV mink lung cells in a serum-containing growth medium, transferring and maintaining said cultured cells in a serum-free medium under conditions and for a time adequate to accumulate in said serum-free medium, said CDV viral precursor immunogens being shed from said cells, and separating said cells from said viral precursor immunogen-containing supernatent. This CDV viral precursor immunogen-containing supernatant then is suitably diluted and blended with a pharmaceutically-acceptable adjuvant for forming the CDV vaccine disclosed herein.

DETAILED DESCRIPTION OF THE INVENTION

The vaccine of the present invention effectively protects dogs against disease associated with CDV. Also, innoculated dogs are not carriers of the disease. This effective protection coupled with the fact that the vaccine is ostensibly virus-free provides obvious advantages for using the inventive vaccine. Finally, the inventive CDV vaccine can be combined with vaccines effective against other canine diseases without prejudicing the efficacy thereof. Other vaccines which can be combined with present CDV vaccine include, for example, vaccines against parvovirus, cornovirus, adenovirus, and parainfluenza.

The viral precursor immunogens derived from the persistently-infected cells are proteins or protein precursors (e.g. unassembled viral proteins) associated with CDV. These immunogens can be collected in serum-free medium from the persistently-infected cells and then formulated into a vaccine which is effective in protecting dogs against disease associated with CDV. Referring initially to the method for harvesting the CDV viral precursor immunogens, the first step requires the selection of a cell line which can be persistently infected with CDV wherein the CDV is non-cytotoxic to the cell line of choice. Also, it is desirable not to sacrifice the cell line for the sake of harvesting the viral precursor immunogens. Thus, the cell line of choice should not only be capable of being persistently infected with CDV, but also should be amenable to the harvesting of viral precursor immunogens followed by recycle to the process for growth and harvesting again.

The cell line of choice yielding the CDV vaccine disclosed herein comprises CCL-64 mink lung cells which have been persistently infected with CDV for producing CCL-64-LyCDV mink lung cells. This cell line has been deposited on Dec. 7, 1988, with the American Type Culture Collection (ATCC) in 1231 Parklawn Drive, Rockville, Md. 20852, and assigned ATT Accession No. CRL 9891.

The CDV persistently-infected mink lung cell line was subjected to chromosome analysis as follows. The cell culture was treated directly with Colcemid, harvested with a trypsin-EDTA solution to release the cells from the flask surface, exposed to a hypotonic solution, fixed with a methanol-glacial acetic acid mixture, and air-dried on microscope slides. The slides were stained with Wright's stain to obtain G-banded preparations. Using a Leitz photomicroscope, visual counts, and analyses were made under $1000 \times$ omagnification. Photomicrographs of representative metaphases were take on an Olympus photomicroscope and karyotypes constructed. A chromosome count performed on a minimum of 50 metaphases from the cell line revealed the following distribution:

| No. Metaphases | 29 | 29 | 30 | 31 | 32 | 60 |
|---|---|---|---|---|---|---|
| No. Chromosomes | 1 | 1 | 34 | 8 | 3 | 3 |
| 1. Modal Chromosome Number: | | | | | | $2n = 30$ |
| 2. Number of Metaphases Analyzed: | | | | | | 50 |
| 3. Number of Metacentrics in Modal Cell Type: | | | | | | 10 |
| 4. Number of Submetacentrics in Modal Cell Type: | | | | | | 12 |
| 5. Number of Acrocentrics in Modal Cell Type: | | | | | | 2 |
| 6. Presence of Dicentric Chromosomes: | | | | | | Yes |
| 7. Presence of Hypomodal Metaphases: | | | | | | Yes |
| 8. Presence of Hypermodal Metaphases: | | | | | | Yes |

As a first step in the process, the invected CCL-64 cells are placed in a serum-containing growth medium for their culturing. Such serum-containing growth medium comprises a conventional serum-free growth medium having added thereto an appropriate quantity of animal serum, such as fetal bovine serum. Appropriate serum-free media include McCoy's 5a medium, RPMI 164 medium, and like conventional media. To such serum-free medium are added appropriate quantities of serum and antibiotics in conventional fashion. The cells are cultured in such medium, with additional serum optionally added from time to time, preferably until such cells have reached saturation density in the volume of medium used. Conventional growth conditions are maintained as such conditions are well known in the art.

The next step of the process comprises transferring the cultured persistently-infected cells to a serum-free growth medium of composition desirably substantially the same as that used in the culturing step of the process, except that no serum is used or added during this step of the process. The cells placed in the serum-free medium apparently cease their normal growth cycle and virtually all viral production is arrested. The cells are subjected to severe stress in the serum-free medium so that an abundance of viral precursor immunogens (and possibly additional cell matter) are shed from the cells in substantial quantities.

The supernatant comprising serum-free medium containing viral precursor immunogens then is separated from the persistently-infected cells by conventional separation techniques including, for example, centrifugation. The separated cell line then can be recycled to the culturing step of the process optionally innoculated with fresh persistently-infected cells.

The first medium-containing CDV viral precursor immunogens may be lyophilized or can be converted into a vaccine immediately. If lyophilization is the technique of choice, the viral precursor immunogen powder can be stored in such form or can be resuspended and stored at very low temperatures (e.g. $-90°-0°$ C.) as is necessary, desirable, or convenient.

In order to illustrate the cell proclivity for CDV viral precursor immunogen production, the following typical growth curve is set forth below.

| Days Post First Fluid Change | Period Between Harvests | ELISA Antigen Units/0.05 ML Average |
|---|---|---|
| 1 | Daily Harvests | 2,031 |
| 2 | | 3,941 |
| 3 | | 5,055 |
| 4 | | 6,285 |
| 7 | | 37,740 |
| 2 | Harvest Every Two Days | 7,027 |
| 4 | | 14,7777 |
| 7 | | 24,204 |
| 3 | Harvest Every Three Days | 12,208 |
| 7 | Days | 21,508 |

In order to convert the CDV viral precursor immunogens into a vaccine which is effective for the prevention of disease caused by CDV, the CDV viral precursor immunogen supernatant advantageously is diluted, preferably with water, and blended with a pharmaceutically-acceptable adjuvant. As the data establishes, the CDV viral precursor immunogen concentration in the supernatant separated from the CDV persistently-infected cells can be diluted on up to about 1:28 (volumetric ratio) and still an immune response is evoked in dogs vaccinated therewith, though dilutions of about 1:14 to 1:20 presently appear to be advantageous in this regard. The determination of the CDV viral precursor immunogen concentration supernatant separated from the harvested infected cells conveniently can be determined by a conventional ELISA procedure utilizing polyclonal or monoclonal antibody. Thereafter, pharmaceutically, acceptable adjuvants are added in conventional amounts to the diluted CDV viral precursor immunogen serum-free medium. Convenient adjuvants include, for example, oil-in-water, aluminum hydroxide, Quil A, EMA, DDA, TDM-Squalene, lecithin, alum, saponin, and the like and even mixtures thereof.

The vaccine as-prepared or in combination with other canine vaccines or inoculants can be used to inoculate canines for the prevention of disease associated with CDV. As noted above, viral precursor immunogen units per dosage then are administered to canine by conventional routes of administration, e.g. parenteral inoculation including subcutaneous and intramuscular vaccination. The age at which canines should be inoculated with the inventive vaccine is consistent with the use of present vaccines, e.g. about 6 to 16 weeks of age desirably.

The following examples show how the present invention has been practiced but should not be construed as limiting. All units herein are in the metric system unless otherwise expressly indicated and all references cited herein are incorporated expressly herein by reference.

EXAMPLES

Example 1

The persistently-infected CCL-64 mink lung cell line disclosed herein was propagated at 37° C. in Eagles minimum essential medium supplemented with 10% fetal bovine serum. Bovine-free media from the confluent monolayers of the persistently-infected cell line was frozen and thawed, and any residual virus inactivated using 1 mM binary ethylene imine at 4° C. After inactivation, the fluid was divided into three aliquots and each adjuvanted differently: the first alliquot with Quil A; the second aliquot with EMA; and the third aliquot with oil of lecithin.

12 CDV seronegative dogs were divided into three groups. Each of the three groups of dogs received two subcutaneous vaccinations (1 ml) three weeks apart. The only difference between the three groups was the different adjuvant used in the vaccine preparation. Blood samples were collected prior to each vaccination and at the time of challenge (two weeks post second vaccination). Sera from the bleedings were used for determination of antibody titers to CDV. At two weeks post second vaccination, all vaccinates plus two control dogs each were challenged intranasally with virulent CDV. Clinical observations and recording of body temperature of the test dogs were determined daily.

The technique used for serological determinations of CDV neutralizing tests in Vero cells with the adapted Onderstepoort strain of CDV. Virus neutralizing (VN) titers were expressed as the reciprocal of the highest dilution of serum which caused complete virus neutralization. The results are set forth below:

TABLE I

| Clinical Observations Post-Challenge Temperature (°F.) | | | | | | | | |
|---|---|---|---|---|---|---|---|---|
| | Days Post Challenge | | | | | | | |
| Dog | 0 | 1 | 2 | 3 | 4 | 5 | 6 | 7 |
| Group 1 | | | | | | | | |
| 4502 | 102.0 | 102.8 | 101.6 | 101.1 | 100.7 | 100.6 | 101.1 | 100.1 |
| 4262 | 101.1 | 101.4 | 101.1 | 101.0 | 101.6 | 100.3 | 100.9 | 102.1 |
| 4263 | 103.0 | 103.1 | 101.2 | 101.7 | 100.5 | 100.4 | 101.6 | 102.4 |
| 4264 | 101.1 | 101.4 | 101.1 | 101.0 | 101.6 | 100.3 | 100.9 | 102.1 |
| Avg- | 101.8 | 102.2 | 101.3 | 101.2 | 101.1 | 100.4 | 101.1 | 101.7 |
| Group 2 | | | | | | | | |

TABLE I-continued

Clinical Observations Post-Challenge Temperature (°F.)

| Dog | | | | | | | |
|---|---|---|---|---|---|---|---|
| 4233 | 101.6 | 102.4 | 101.8 | 101.5 | 101.4 | 101.7 | 101.4 | 101.4 |
| 4234 | 102.4 | 102.1 | 101.0 | 100.9 | 101.0 | 101.6 | 101.4 | 100.8 |
| 4328 | 102.2 | 101.8 | 101.0 | 101.1 | 102.1 | 101.6 | 101.1 | 101.9 |
| 4330 | 102.3 | 102.4 | 101.6 | 101.2 | 101.5 | 100.9 | 101.0 | 102.1 |
| Avg-Group 3 | 102.1 | 102.2 | 101.4 | 101.2 | 101.5 | 101.5 | 101.2 | 101.6 |
| 4199 | 101.6 | 102.2 | 101.1 | 100.0 | 100.4 | 100.6 | 101.4 | 102.0 |
| 4200 | 101.3 | 101.0 | 101.1 | 100.4 | 100.5 | 100.0 | 99.9 | 101.4 |
| 4316 | 103.0 | 102.2 | 100.3 | 100.4 | 100.1 | 100.4 | 100.4 | 101.1 |
| 4335 | 103.0 | 102.8 | 101.0 | 102.6 | 101.3 | 101.2 | 102.3 | 103.1 |
| Avg-Controls | 102.2 | 102.1 | 100.9 | 101.1 | 100.6 | 100.6 | 101.0 | 101.9 |
| 4333 | 100.3 | 102.1 | 100.5 | 101.4 | 104.3 2 | 104.3 1,4 | 102.6 | 102.6 |
| 4334 | 101.6 | 101.8 | 100.7 | 102.2 | 102.4 | 105.6 | 102.2 | 102.4 |
| Avg- | 101.0 | 102.0 | 100.6 | 101.8 | 103.4 | 105.0 | 102.4 | 102.5 |

Days Post Challenge

| Dog | 8 | 9 | 10 | 11 | 12 | 13 | 14 |
|---|---|---|---|---|---|---|---|
| Group 1 | | | | | | | |
| 4502 | 100.5 | 100.2 | 100.7 | 100.8 | 100.4 | 100.7 | 101.6 |
| 4262 | 100.9 | 101.0 | 101.4 | 101.5 | 102.0 | 100.2 | 100.8 |
| 4263 | 100.7 | 101.6 | 101.3 | 101.0 | 101 | 100.8 | 101.3 |
| 4264 | 100.9 | 101.0 | 101.4 | 101.5 | 102 | 100.2 | 100.8 |
| Avg-Group 2 | 100.8 | 101.0 | 101.2 | 101.2 | 101.4 | 100.5 | 101.1 |
| 4233 | 102.1 | 101.7 | 101.7 | 101.7 | 101.6 | 100.4 | 101.1 |
| 4234 | 100.6 | 101.2 | 101.4 | 102.2 | 101.0 | 101.4 | 101.0 |
| 4328 | 101.7 | 102.1 | 102.0 | 102.2 | 101.8 | 100.4 | 101.5 |
| 4330 | 100.8 | 102.1 | 100.8 | 101.9 | 101.0 | 100.6 | 100.1 |
| Avg-Group 3 | 101.3 | 101.8 | 101.5 | 102 | 101.4 | 100.7 | 100.9 |
| 4199 | 100.9 | 100.9 | 101.1 | 101.6 | 100.9 | 100.2 | 101.2 |
| 4200 | 101.0 | 101.5 | 100.1 | 101.2 | 100.4 | 100.4 | 101.1 |
| 4316 | 100.9 | 100.5 | 100.5 | 101.1 | 101.3 | 100.4 | 101.0 |
| 4335 | 102.2 | 101.2 | 101.4 | 100.9 | 101.0 | 100.2 | 100.5 |
| Avg-Controls | 101.3 | 101.0 | 100.8 | 101.2 | 100.9 | 100.3 | 101.0 |
| 4333 | 101.8 | 101.8 3 | 101.8 3 | 102.6 4 | 101.4 4 | 101.7 1,4,5 | 102.3 1,4,5 |
| 4334 | 101.3 | 102.3 | 102.5 | 103.2 | 103.1 | 103.1 | 104.6 |
| Avg- | 101.6 | 102.1 | 101.7 | 102.9 | 102.3 | 102.4 | 103.5 |

Days Post Challenge

| Dogs | 15 | 16 | 17 | 18 | 19 | 20 | 21 |
|---|---|---|---|---|---|---|---|
| Group 1 | | | | | | | |
| 4502 | 100.7 | 101.0 | 100.1 | 100.9 | 100.9 | 101.0 | 101.3 |
| 4262 | 101.7 | 102.0 | 101.8 | 102.1 | 101.0 | 101.1 | 101.1 |
| 4263 | 101.6 | 101.7 | 101.8 | 101.8 | 102.0 | 101.9 | 100.9 |
| 4264 | 100.6 | 100.7 | 101.6 | 101.7 | 101.7 | 101.5 | 101.6 |
| Avg-Group 2 | 101.2 | 101.4 | 101.3 | 101.6 | 101.4 | 101.4 | 101.2 |
| 4233 | 101 | 101.5 | 101.7 | 101.6 | 101.8 | 101.6 | 101.4 |
| 4234 | 101.4 | 101.4 | 100.9 | 101.2 | 101.1 | 101.2 | 102.1 |
| 4328 | 100.9 | 101.4 | 101.8 | 101.8 | 101.8 | 101.8 | 101.8 |
| 4330 | 100.2 | 101 | 101 | 101 | 101.3 | 101.1 | 101.5 |
| Avg-Group 3 | 100.9 | 101.3 | 101.4 | 101.4 | 101.5 | 101.4 | 101.7 |
| 4199 | 100.7 | 101.2 | 101.2 | 101.1 | 101.1 | 101.3 | 101.0 |
| 4200 | 100.5 | 101.3 | 101.0 | 101.1 | 101.7 | 101.8 | 101.1 |
| 4316 | 100.5 | 101.4 | 101.3 | 101.5 | 101.5 | 101.5 | 101.1 |
| 4335 | 100.7 | 101.6 | 101.3 | 101.8 | 101.3 | 101.3 | 101.3 |
| Avg-Controls | 100.6 | 101.4 | 101.2 | 101.4 | 101.4 | 101.5 | 101.1 |
| 4333 | 101.7 1,5 | 102.8 1,5 | 101.9 1,5 | 101.8 | 102.3 | 102 | 101.5 |
| 4334 | 101.7 | 102.3 | 102.1 | 102.2 | 101.3 | 101.9 | 102.0 |
| Avg- | 101.7 | 102.6 | 102.0 | 102.0 | 101.8 | 102.0 | 101.8 |

Clinical Observation Key:
No mark = normal
1 = depressed
2 = mucus/tarry stools
3 = diarrhea
4 = bloody diarrhea
5 = thin/not eating

TABLE 2

CANINE DISTEMPER POTENCY TEST

| Group | Dog No. | VN TITER Pre Vacc | Pre 2-Vacc | Pre CHALL |
|---|---|---|---|---|
| 1 | 4502 | 0 | 8 | 16 |
| | 4262 | 0 | 16 | 16 |
| | 4263 | 0 | 8 | 32 |
| | 4264 | 0 | 4 | 16 |
| Geometric Mean Titer | | 0 | 8 | 19.0 |
| 2 | 4233 | 0 | 8 | 16 |
| | 4234 | 0 | 8 | 16 |
| | 4328 | 0 | 2 | 32 |
| | 4330 | 0 | 8 | 32 |
| Geometric Mean Titer | | 0 | 2 | 16 |
| 3 | 4199 | 0 | 2 | 16 |
| | 4200 | 2 | 8 | 8 |
| | 4316 | 0 | 4 | 16 |
| | 4335 | 0 | 2 | 16 |
| Geometric Mean Titer | | 1.2 | 3.4 | 13.5 |
| Controls | 4333 | 0 | 0 | 0 |
| | 4334 | 0 | 0 | 0 |
| Geometric Mean Titer | | 0 | 0 | 0 |

The results set forth at Table 1 indicate that two non-immunized dogs contracted severe disease after challenge with virulent CDV. Both dogs became severely depressed with bloody diarrhea and noted weight loss. The temperature profiles from these two dogs showed the typical biphasic curve, typical of virulent CDV. In contrast, dogs immunized with the different adjuvanted vaccine preparations of the present invention did not show any symptoms or exhibit an elevated temperature response post-challenge.

As the results set forth in Table 2 indicate, all dogs in each adjuvant group responded serologically with VN titers prior to challenge. The control dogs remained serologically negative prior to challenge.

Example 2

In order to generate data on a minimum immunizing dose study, the concentration of CDV viral precursor immunogens in the separated supernatant needed to be ascertained. The following ELISA procedure for vaccine antigen (CDV viral precursor immunogens) quantitation was utilized. The Ig-G fraction of canine distemper antisera (caprine origin) was separated and divided into 0.5–1.0 ml aliquots and frozen for use as the polyclonal antibody in the ELISA procedure. Plates were prepared by coating Immulon II plates (Dynatec) with the fractionated Ig-G at a 1:60 dilution ratio in borate buffer. The quantity of fractionated Ig-G utilized was 0.1 ml for 96 well plates. The plates were sealed with sealing tape and "floated" in a 37° C. water bath for 1.5 hours and then stored under refrigeration at 4° C. for at least 24 hours. These plates may be stored for up to two weeks before use.

In use, the plates are rinsed three times with PBS-Tween buffer with a 3 minute soak between washes.

The standard antigen for the test is diluted in PBS-Tween buffer containing 1% BSA. The standard antigen is tested at 1:4, 1:8, 1:16, 1:32, 1:64, and 1:128 dilutions. Next, a 0.05 ml of PBS with 1% BSA is added to each well on the plate. To appropriate wells then is added 0.05 ml of the vaccine sample, the standard antigen or reference antibody. A minimum of four wells per sample is used. Additionally, a minimum of four wells are used as blanks and are filled with 0.05 ml of PBS with 1% BSA. The plates are shaken on a microtiter shaker for 20 seconds. The plates then are sealed with sealing tape and floated in 37° C. water bath for one hour. After incubation, the plates are rinsed three times with PBS-Tween buffer with a 3 minute soak between washes. To each vaccine sample and blank well then is added 0.01 ml of ammonium sulfate precipitated dog anti-CD immunoglobulin diluted 1:500 in PBS-Tween buffer with 1% BSA. All antigens common to capture and the second antibody are quantitated. Both are polyclonal and this test method is used to quantitate the mid-test antigen (viral precursor immunogen) concentration. When using a polyclonal-monoclonal (HA) system, the monoclonal antibody prepared from the Ig-G fraction of an Ig-M/Ig-G isolation is diluted 1:1000 in PBS-Tween buffer containing 1% BSA and the HA antigen quantitated.

Thereafter, the plates again are sealed with sealing tape and floated in 37° C. water bath for one hour. After incubation, the plates are rinsed three times with PBS-Tween buffer with 3 minute soak between washes. To each well including the blank wells is added 0.1 ml of alkaline phosphatase labeled anti-dog Ig-G (L and H chain) diluted 1:1000 in Brain Heart Infusion Broth or alkaline phosphatase labeled anti-mouse Ig-G (L and H) chain for the polyclonal-monoclonal system. Again, the plates are sealed with sealing tape, floated in a 37° C. water bath for one hour. After incubation, the plates are rinsed three times with PBS-Tween buffer with a 3 minute soak between washes. To each well including the blank wells then is added 0.1 ml of n-nitrophenyl phosphate substrate diluted in diethanol amine buffer. The plates again are sealed with sealing tape and incubated at room temperature for 20 minutes for the polyclonal-polyclonal system or floated in 37° C. water bath for 45-60 minutes for the polyclonal-monoclonal system.

When the desired optical density is reached, the reaction is stopped by the addition of 0.1 ml of 3N NaOH to each well. The optical densities of each wells are read on a spectrophotometer in the dual mode with the test wavelength being 410 nm and the reference wavelength at 490 nm. The average of the blank wells is subtracted from the average of the sample wells.

For the polyclonal-polyclonal system, a linear regression analysis is used to generate a standard Antigen Unit curved by plotting the blanked optical density averages of the standard antigen versus $Log_{10}$ of the antigen concentrations given below. For the polyclonal-monoclonal system, a quadratic regression analysis is used to generate a standard Antigen Unit curve by plotting the balanced CD average of the standard antibody versus $Log_{10}$ of the antibody concentration.

Regardless of the technique used (polyclonal or monoclonal system), the following standard dilution versus concentration curve was determined.

| Dilution of Standard | Concentration |
|---|---|
| 1:4 | 3200 |
| 1:8 | 1600 |
| 1:18 | 800 |
| 1:32 | 400 |
| 1:64 | 200 |
| 1:128 | 100 |

From the standard Antigen Unit curve which can be plotted from the foregoing data, the concentration of any unknown test sample can be determined.

Based on the foregoin ELISA test procedure, minimum immunizing dose studies were conducted in seronegative dogs. The vaccine was prepared as described in connection with Example 1 utilizing aluminum hydroxide as the adjuvant.

Eight seronegative dogs were divided into three groups. Each of the three groups of dogs received two subcutaneous vaccinations three weeks apart. The only difference between the three groups was that the concentration of CDV viral precursor immunogens used in the vaccine was different. Blood samples were collected prior to each vaccination and at the time of challenge (two weeks post-second vaccination). Sera from the bleedings were used for determination of antibody titers to CDV. At two weeks post-second vaccination, all vaccinates plus three control dogs each were challenged intracereberally with virulent CDV. Clinical observations of the test dogs were determined daily during the post challenge period. Again, the Viral Neutralizing titers were determined as described in connection with Example 1. The following data was recorded:

TABLE 3

| | | Serum Antibody Titer | | |
|---|---|---|---|---|
| Dog No. | Antigen Units | Pre-Vac. | Pre-2nd Vac. | Pre-Chall. |
| G-182 | 500 | Neg. | 2 | 16 |
| G-210 | | Neg. | 0 | 32 |
| | Geometric Mean | — | 1 | 23 |
| G-181 | 1000 | Neg. | 0 | 32 |
| G-204 | | Neg. | 2 | 128 |
| G-214 | | Neg. | 2 | 64 |
| | Geometric Mean | — | 2 | 64 |
| G-180 | 2000 | Neg. | 2 | 64 |
| G-208 | | Neg. | 0 | 64 |
| G-213 | | Neg. | 2 | 64 |
| | Geometric Mean | — | 2 | 64 |
| G-176 | Contact Controls | Neg. | Neg. | Neg. |
| G-183 | | Neg. | Neg. | Neg. |
| G-215 | | Neg. | Neg. | Neg. |
| | Geometric Mean | — | — | — |

TABLE 4

Minimum Immunizing Dose Study
Clinical Observations

| Dog No. | Antigen Amount | Days Post Challenge 1 | 2 | 3 | 4 | 5 | 6 |
|---|---|---|---|---|---|---|---|
| G-182 | 500 | All vaccinates remained normal. | | | | | |
| G-210 | | | | | | | |
| G-181 | 1000 | | | | | | |
| G-204 | | | | | | | |
| G-214 | | | | | | | |
| G-180 | 2000 | | | | | | |
| G-208 | | | | | | | |
| G-213 | | | | | | | |
| G-187 | Contact | 1* | 1 | 1 | 1 | 1 | 1 |
| G-183 | Controls | 1 | 1 | 1 | 1 | 1 | 1 |
| G-215 | | 1 | 1 | 1 | 1 | 1 | 1 |

TABLE 4-continued Minimum Immunizing Dose Study
Clinical Observations

| Dog No. | Antigen Amount | Days Post Challenge 7 | 8 | 9 | 10 | 11 |
|---|---|---|---|---|---|---|
| G-182 | 500 | All vaccinates remained normal. | | | | |
| G-210 | | | | | | |
| G-181 | 1000 | | | | | |
| G-204 | | | | | | |
| G-214 | | | | | | |
| G-180 | 2000 | | | | | |
| G-208 | | | | | | |
| G-213 | | | | | | |
| G-187 | Contact | 1 | 1 | 1 | 2,5 | 2,4 |
| G-183 | Controls | 1 | 1 | 1 | 2,3 4 | 2,3 4 |
| G-215 | | 1 | 1 | 1 | 2,3 4 | 2,3 4 |

| Dog No. | Antigen Amount | Days Post Challenge 12 | 13 | 14 | 15 | 16 |
|---|---|---|---|---|---|---|
| G-182 | 500 | All vaccinates remained normal. | | | | |
| G-210 | | | | | | |
| G-181 | 1000 | | | | | |
| G-204 | | | | | | |
| G-214 | | | | | | |
| G-180 | 2000 | | | | | |
| G-208 | | | | | | |
| G-213 | | | | | | |
| G-187 | Contact | 2 | 2 | 1 | 1 | 1 |
| G-183 | Controls | 2,4 | 2,4 | 2 | 2 | 2 |
| G-215 | | 2,4 | 2,4 | 2 | 2 | 2 |

| Dog No. | Antigen Amount | Days Post Challenge 17 | 18 | 19 | 20 | 21 |
|---|---|---|---|---|---|---|
| G-182 | 500 | All vaccinates remained normal | | | | |
| G-210 | | | | | | |
| G-181 | 1000 | | | | | |
| G-204 | | | | | | |
| G-214 | | | | | | |
| G-180 | 2000 | | | | | |
| G-208 | | | | | | |
| G-213 | | | | | | |
| G-176 | Contact | 1 | 1 | 1 | 1 | 1 |
| G-183 | Controls | 1 | 1 | 1 | 1 | 1 |
| G-215 | | 1 | 1 | 1 | 1 | 1 |

*Clinical Observation Key:
1 = normal
2 = depressed
3 = vomiting
4 = diarrhea
5 = CNS Symptoms The above-tabulated results indicate that there was little significant difference between the VN titers of the groups of dogs receiving vaccine containing different amounts of CDV viral precursor immunogens (antigens). At the time of challenge, the 1000 unit stimulated as good of a serological response as the 2000 unit vaccine. Antibody response to the 500 unit vaccine was lower than that for the other two vaccines, indicating that this vaccine contained less CDV viral precursor immunogens (antigens) and, therefore, was less potent. These data indicate that the CDV viral precursor immunogens can be diluted and standardized for a potent CDV vaccine. The sentinal control dogs remained negative during the vaccination period indicating that the vaccinate and control dogs were never exposed to CDV prior to challenge.

As the clinical observation at data in Table 4 indicates, all vaccinates were protected against clinical symptoms associated with virulent challenge CDV. The vaccine containing 500 units protected the dogs against challenge virus as well as the vaccines containing higher amounts of CDV viral precursor immunogens. All control dogs exhibited typical signs of CDV, ranging from depression to central nervous system involvement.

I claim:

1. Canine distemper virus (CDV) vaccine for the immunization of CDV susceptible canine comprising an ostensibly virus-free immunizing-effective amount of:

(a) CDV immunogens which are derived from CDV persistently-infected cells cultured in vitro and then separated from said in vitro cultured CDV peristently-infected cells and (b) a pharmaceutically-acceptable adjuvent.

2. The CDV vaccine of claim 1 wherein said CDV persistently-infected cells comprise CCL-64 mink lung cells.

3. The CDV vaccine of claim 1 wherein said CDV immunogens are harvested from serum-free growth medium.

4. The CDV vaccine of claim 3 wherein said CDV persistently-infected cells are cultured in serum-containing growth medium and then transferred to said serum-free growth medium.

5. The CDV vaccine of claim 2 wherein said CDV persistently-infected cells are from cell line ATCC number CRL9891.

6. A process for immunizing canine distemper virus (CDV) susceptible canine comprising parenterally inoculating said canine with the vaccine of claim 1.

7. The process of claim 6 wherein said canine 6 to 16 weeks of age when inoculated.

8. The process of claim 6 wherein said canine is inoculated with the vaccine of claim 5.

9. The process of claim 6 wherein said pharmaceutically-acceptable adjuvant is selected from the group consisting of oil-in-water, aluminum hydroxide, Quil A, dimethyldioctadecylammonium bromide (DDA), trehalose dimycolate-Squalene, (TDA-Squalene), lecithin, alum, saponin, and mixtures thereof.

* * * * *